US00PP19465P2

(12) United States Plant Patent
Austin

(10) Patent No.: US PP19,465 P2
(45) Date of Patent: Nov. 18, 2008

(54) ***ROSA HYBRIDA* SHRUB NAMED 'AUSPRIOR'**

(50) Latin Name: *Rosa hybrida*
Varietal Denomination: AUSprior

(75) Inventor: David C. H. Austin, Wolverhampton (GB)

(73) Assignee: David Austin Roses Ltd., Wolverhampton (GB)

( * ) Notice: Subject to any disclaimer, the term of this patent is extended or adjusted under 35 U.S.C. 154(b) by 0 days.

(21) Appl. No.: 12/001,118

(22) Filed: Dec. 10, 2007

(51) Int. Cl.
*A01H 5/00* (2006.01)

(52) U.S. Cl. ..... Plt./103

(58) Field of Classification Search ..... Plt./103
See application file for complete search history.

*Primary Examiner*—Annette H Para
(74) *Attorney, Agent, or Firm*—Kauth, Pomeroy, Peck & Bailey LLP

(57) ABSTRACT

A variety of rose plant of the shrub class, named 'AUSprior'. The 'AUSprior' rose is a plant suitable for repeat flowering production having creamy-white blooms and a strong myrrh fragrance.

1 Drawing Sheet

Classification: The present invention relates to a new *Rosa hybrida* shrub.

Variety Denomination: The new plant has the varietal denomination 'AUSprior'.

ORIGIN OF INVENTION

This invention relates to a new and distinct variety of shrub rose plant named 'AUSprior', which was originated by crossing two unnamed, unpatented varieties of *Rosa hybrida.*

BACKGROUND OF THE INVENTION

The primary objective of this breeding was to produce a very healthy repeat flowering variety having large, creamy-white blooms with a strong myrrh fragrance and strong arching growth.

SUMMARY OF THE INVENTION

Among the features which distinguish the new variety from other presently available and commercial rose cultivars known to the inventor is the following combination of characteristics: large, creamy-white blooms and a strong myrrh fragrance and strong arching growth.

Asexual reproduction of the new variety by budding as performed in greenhouses at Bowling Green Lane in Albrighton, Britain shows that the foregoing and other distinguishing characteristics come true to form and are established and transmitted through succeeding asexual propagations. 'AUSprior' may be asexually propagated by budding and grafting. The budding and grafting successfully occurred on the plant/rootstock *Rosa* cv., 'Dr. Huey' in the United States and on the plant/rootstock *Rosa dumetorum* cv., 'Laxa ' in the United Kingdom.

COMPARISON WITH PARENTS

The new rose may be distinguished from its seed parent, by the following combination of characteristics: whereas the parent has yellow blooms and a tea fragrance, 'AUSprior' bears flowers of creamy-white and a myrrh fragrance. The new variety is classified as a *hybrida* rose with a strong arched growing habit.

The new variety may be distinguished from its pollen parent, by the following combination of characteristics: whereas the pollen parent bears pink blooms, 'AUSprior' bears flowers of a creamy-white.

COMPARISION WITH THE CLOSEST COMMERCIALLY AVAILABLE CULTIVAR

The closest commercially available cultivar to the new variety is the 'AUSrelate' (U.S. Pat. No. 18,702). The new rose may be distinguished from the 'AUSrelate' variety by the following combination of characteristics: the 'AUSrelate' has fewer petals, creamy apricot blooms and semi-glossy leaves compared to 'AUSprior', which has a greater number of petals, creamy-white blooms and matt leaves.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (2001) except where common terms of color definition are employed.

DESCRIPTION OF THE NEW VARIETY

The following description is of 2 year-old rose plants of the new variety grown outdoors in Albrighton, Britain in the month of August. Phenotypic expression may vary with environmental, cultural and climatic conditions, as well as differences in conditions of light and soil.

Flower characteristics:

*Blooming habit.*—Recurrent. The number of blooms per plant during the growing season is profuse, but there are too many to count.

*Bud.*—Size: About 2.5 cm long and 2.5 cm in diameter when the petals start to unfurl. Form: The bud form is globular. Color: When sepals first divide, the bud color is Yellow Group 1C, with red flecks. When half blown, the upper sides of the petals are White Group 155A, and the lower sides of the petals are White Group 155A. Calyx: Shape: (from above) star-shaped. Length: 2 cm. Diameter: 4.5 cm. Sepals: Arrangement: Regular. Color: Upper Surface: Greyed-Green Group 194B. Lower Surface: Yellow-Green Group 144B. Length: 2.3 cm. Width: 1 cm. Shape: Subulate. Margin: Slightly canescent. Surface texture: Upper Surface: Pubescent. Lower Surface: Smooth. Number: There are three normally appendaged sepals. There are 2 unappendaged sepals with hairy edges. Receptacles: Color: Yellow-Green Group 144A. Shape: campanulate. Size: medium, about 1 cm×1 cm. Surface: Smooth. Peduncle: Length: long, averaging about 15 cm. Surface: smooth. Color: Yellow-Green Group 144B. Strength: Strong.

*Blooms.*—Size: Large, average open diameter is about 9 cm. Borne: Singly in clusters of 5–10 blooms having corymb shaped inflorescence. Stems: Strength: Normal, average length is about 50 cm. Diameter: 4 mm. Form: When first open, bloom is cupped. Permanence of bloom: flattens.

*Petalage.*—Number of petals under normal conditions: 120. Color: The upper sides of the petals are White Group 155B. The reverse sides of the petals are White Group 155B. The base of the petals is White Group 155B. Fragrance: Strong. Character of fragrance: Myrrh.

*Petals.*—Texture: Smooth, satiny. Size: Width: 3.3 cm. Length: 4.2 cm. Surface: Smooth. Shape: Obovate. Margin: Notched. Apex Shape: Slightly emarginate. Base Shape: Pointed. Form: Slightly incurved. Arrangement: Informal. Petaloids: Number: 4. Color: Petal: White Group 155A; Anther: Yellow-Orange Group 15A; Filament: Red Group 48B. Length: Petal: 10 mm. Anther: 2.5 mm. Filament: 10 mm. Width: Petal only: 10 mm. Shape: Irregular. Margin: Irregular. Persistence: Petals drop off cleanly before drying. Lastingness: On the plant: fair, about 4–5 days. As a cut flower: not tested.

*Reproductive parts.*—Stamens: Number: 50. Length: 12.5 mm. Anthers: Length: 2.5 mm. Color: Yellow-Orange Group 15A. Arrangement: Tucked in calyx or partly so mixed with petaloids. Filaments: Color: Red Group 48B. Length: 10 mm. Pollen: Color: Yellow-Orange Group 15A. Pistils: Number: 30. Length: 10 mm. Styles: Color: White Group 155D. Length: 9 mm. Stigmas: Color: Yellow Group 8B. Length: 1 mm. Hips: None Observed.

Plant characteristics:

*Plant form.*—Shrub.

*Plant growth.*—Vigorous and arching.

*Age to maturity.*—Two years.

*Mature plant.*—Height: 1.35 m. Width: 0.9 m.

*Rootstock.*—*Rosa* 'Dr. Huey' for U.S. and *Rosa dumetorum* cv. 'Laxa' for observed plants in the U.K.

*Foliage.*—Number: Leaflets on normal mid-stem leaves is: 7 (including terminal leaflet). Size: Medium, about 14.5 cm long×9.5 cm wide. Quantity: Normal. Number of leaves per flowering stem is: 10. Color: New foliage: Upper side: Yellow-Green Group 144A with Greyed-Purple Group 181A around margin. Lower side: Yellow-Green Group 146B with red tinge (not concentrated enough to determine color code). Old foliage: Upper side: Green Group 137A. Lower side: Greyed-Green Group 191A.

*Leaflets.*—Size: About 5 cm long×3 cm wide. Shape: Oval. Base Shape: Obtuse. Apex Shape: Cuspidate. Texture: Leathery. Edge: Serrated. Serrations: Single. Petiole: Color: Green Group 138A. Length: 4 cm. Width: 2 mm. Surface Texture: Prickly. Petiole Rachis: Color: Green Group 138A. Underside: with prickles. Stipules: Length: 2.5 cm, serrated. Color: Green Group 146B. Auricle: Shape: Falcate. Length: 10 mm. Width: 2 mm at base tapering to point. Color: Yellow-Green Group 146B. Vein Color: Green Group 137A. Venation Pattern: Reticulate.

*Wood.*—New Wood: Color: Greyed-Red Group 181A. Bark: Smooth. Old Wood: Color: Yellow-Green Group 144A. Bark: Smooth.

*Branching habit.*—Number: 3 per main stem. Lateral Branch Dimensions: Length: 40 cm. Diameter: 3 mm.

*Stems.*—Mature Stem: Length: 75 cm. Diameter: 4 mm. Internode Distance: 5 cm. The above measurements are all variable, depending on growing conditions in a season. Stem Pubescence Present: No.

*Prickles.*—Quantity: On main canes from base: ordinary. Number per stem length: 4 per 10 cm. On laterals from main canes: few. Number per stem length: 2 per 10 cm. Form: Hooked downward. Length: 5–9 mm. Color when young: Greyed-Purple Group 184A. Color when mature: Greyed-Orange Group 177A and some Greyed-Orange Group 165D.

*Small prickles.*—Quantity: Main stalk: None.

*Disease resistance.*—Mildew: Resistant. Blackspot: Resistant. Rust: Resistant.

*Pest resistance.*—Not tested.

*Winter hardiness.*—Not tested.

*Growing conditions.*—Normal.

What is claimed is:

1. A new and distinct variety of rose plant of the shrub class suitable for repeat flower production, substantially as herein shown and described.

* * * * *

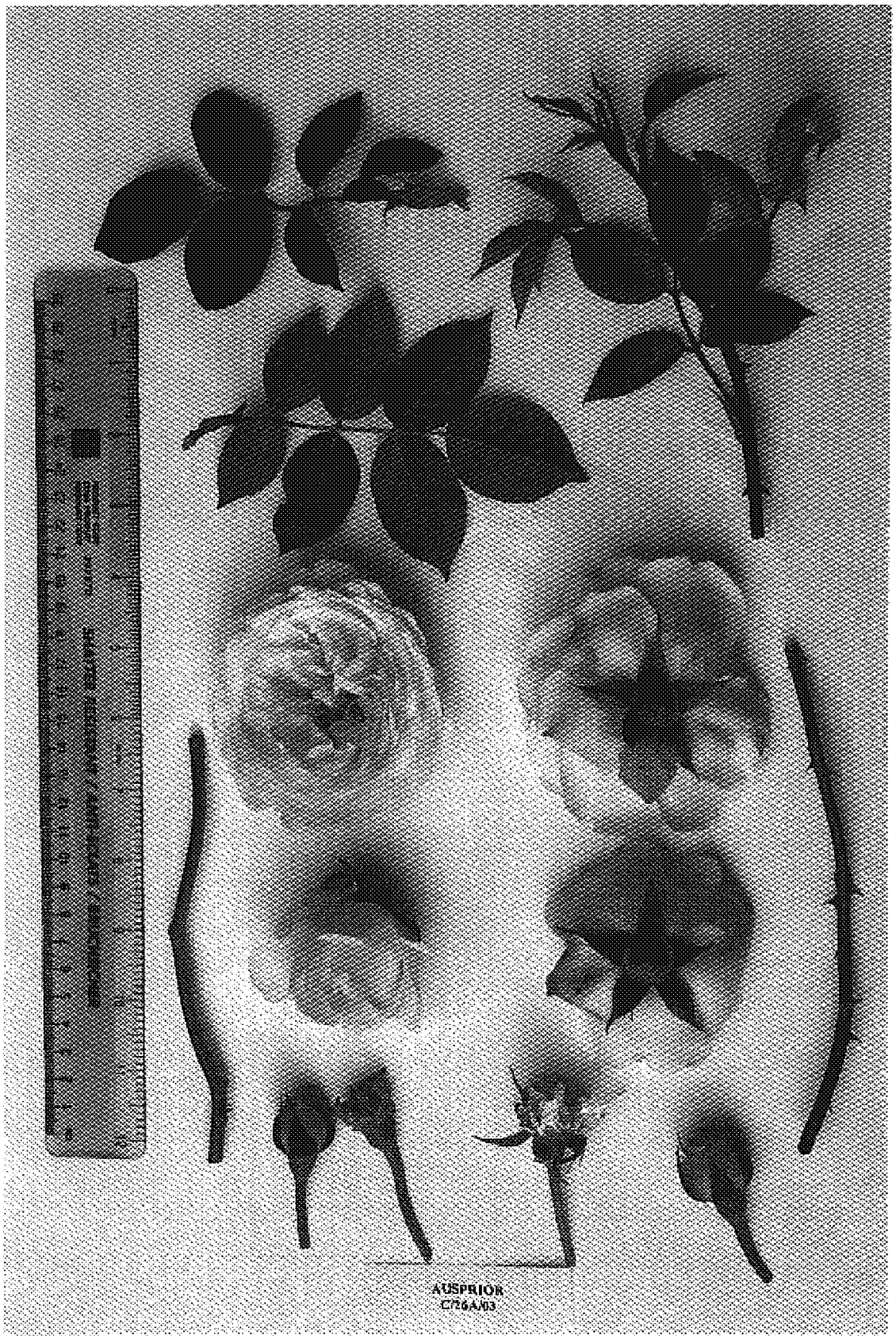
AUSPRIOR
C726A03